US012622672B2

(12) United States Patent    (10) Patent No.:   US 12,622,672 B2

Ramachandran et al.      (45) Date of Patent:    May 12, 2026

---

(54) FIBER-OPTIC REALSHAPE SENSOR FOR ENHANCED DOPPLER MEASUREMENT DISPLAY

(71) Applicant: KONINKLIJKE PHILIPS N.V., Eindhoven (NL)

(72) Inventors: Bharat Ramachandran, Eindhoven (NL); Emil George Radulescu, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 2383 days.

(21) Appl. No.: 15/746,035

(22) PCT Filed: Jul. 14, 2016

(86) PCT No.: PCT/IB2016/054193

§ 371 (c)(1),
(2) Date: Jan. 19, 2018

(87) PCT Pub. No.: WO2017/013539

PCT Pub. Date: Jan. 26, 2017

(65) Prior Publication Data

US 2018/0199914 A1     Jul. 19, 2018

Related U.S. Application Data

(60) Provisional application No. 62/195,333, filed on Jul. 22, 2015.

(51) Int. Cl.
*A61B 8/00*       (2006.01)
*A61B 5/00*       (2006.01)
(Continued)

(52) U.S. Cl.
CPC ............ *A61B 8/4263* (2013.01); *A61B 5/489* (2013.01); *A61B 8/06* (2013.01); *A61B 8/065* (2013.01);
(Continued)

(58) Field of Classification Search
CPC ....... A61B 8/4263; A61B 8/12; A61B 8/0891; A61B 8/4416; A61B 34/20; A61B 5/489;
(Continued)

(56) References Cited

U.S. PATENT DOCUMENTS 5,505,204 A    4/1996   Picot et al.
5,701,898 A    12/1997   Adam et al.
(Continued)

FOREIGN PATENT DOCUMENTS

EP      2550919 A1    1/2013
JP      2003102729 A1   4/2003
WO     2012117337 A1   9/2012

OTHER PUBLICATIONS

Hartley et al. "Doppler velocity measurements from large and small arteries of mice"; Am J Physiol Heart Circ Physiol. Aug. 2011; 301(2): H269-H278 (Year: 2011).*
(Continued)

*Primary Examiner* — Keith M Raymond
*Assistant Examiner* — Amy Shafqat

(57)        ABSTRACT

A Doppler ultrasound system for executing Doppler ultrasound tests. The Doppler ultrasound system employs an ultrasound probe (40), a vessel FORS sensor (20) and a Doppler ultrasound controller (60). In operation, an ultrasound probe (40) transmits an ultrasound beam through a bodily vessel (e.g., a blood vessel) for generating imaging data illustrative of an ultrasound image of fluid flow through the bodily vessel (e.g., blood flow through a blood vessel), and the vessel FORS sensor (20) is introduced into the
(Continued)

bodily vessel for generating vessel sensing data informative of a reconstructed shape of the vessel FORS sensor (20) within the bodily vessel relative to the ultrasound probe (40). Responsive to the data, the Doppler ultrasound controller (60) estimates a parametric relationship between the fluid flow through the bodily vessel and a transmission by the ultrasound probe (40) of the ultrasound beam through the bodily vessel.

14 Claims, 5 Drawing Sheets

(51) Int. Cl.
| | |
|---|---|
| *A61B 8/06* | (2006.01) |
| *A61B 8/08* | (2006.01) |
| *A61B 8/12* | (2006.01) |
| *A61B 34/20* | (2016.01) |
| *A61B 90/00* | (2016.01) |

(52) U.S. Cl.
CPC .............. *A61B 8/0891* (2013.01); *A61B 8/12* (2013.01); *A61B 8/4416* (2013.01); *A61B 8/488* (2013.01); *A61B 34/20* (2016.02); *A61B 8/58* (2013.01); *A61B 2034/2061* (2016.02); *A61B 2090/063* (2016.02); *A61B 2090/067* (2016.02)

(58) Field of Classification Search
CPC ........... A61B 8/065; A61B 8/06; A61B 8/488; A61B 8/58; A61B 2034/2061; A61B 2090/063; A61B 2090/067; A61B 1/0058; A61B 1/0615; A61B 1/07; A61B 1/00059; A61B 1/00167; A61B 2090/364; A61B 2090/378; A61B 1/00165
See application file for complete search history.

(56) References Cited

U.S. PATENT DOCUMENTS

| | | | |
|---|---|---|---|
| 7,850,614 B2 | 12/2010 | Haldeman | |
| 2004/0067000 A1* | 4/2004 | Bates ..................... | A61B 5/742 |
| | | | 385/37 |
| 2008/0221419 A1 | 9/2008 | Furman | |
| 2009/0048518 A1 | 2/2009 | Furman | |
| 2011/0263985 A1* | 10/2011 | Gauthier .............. | A61B 8/0833 |
| | | | 600/454 |
| 2014/0024944 A1 | 1/2014 | Shau et al. | |
| 2014/0155737 A1* | 6/2014 | Manzke .............. | A61B 8/5261 |
| | | | 600/417 |
| 2014/0257095 A1 | 9/2014 | Kemp et al. | |
| 2016/0066794 A1 | 3/2016 | Klinder et al. | |

OTHER PUBLICATIONS

Deloach et al., "Vascular Stiffness: Its Measurement and Significance for Epidemiologic and Outcome Studies"; CJASN Jan. 2008, 3 (1) 184-192 (Year: 2008).*

Kenwright et al. "Assessment of Spectral Doppler for an Array-Based Preclinical Ultrasound Scanner Using a Rotating Phantom", Ultrasound in Medicine & Biology, vol. 41, Issue 8, pp. 2232-2239, Available online May 6, 2015, Version of Record Jun. 10, 2015. (Year: 2015).*

Zettinig et al., 3D velocity field and flow profile reconstruction from arbitrarily sampled Doppler ultrasound data, Med Image Comput Comput Assist Interv . 2014;17(Pt 2):611-8 (Year: 2014).*

Szabo, Chapter 10 from Diagnostic Ultrasound Imaging: Inside Out, Elsevier inc., 2014, pp. 365-430 (Year: 2010).*

* cited by examiner

FIBER-OPTIC REALSHAPE SENSOR FOR ENHANCED DOPPLER MEASUREMENT DISPLAY

FIELD OF THE INVENTION

The present disclosure generally relates to Doppler measurements of fluid flow through a bodily vessel of a patient (e.g., blood flow through a vasculature arrangement of blood vessels within the patient). The present disclosure specifically relates to a novel and inventive pairing of an ultrasound probe and a Fiber-Optic RealShape ("FORS") sensor for enhancing the Doppler imaging of blood flow through a blood vessel (e.g., an artery, a vein or a heart valve).

BACKGROUND OF THE INVENTION

Doppler ultrasound is a non-invasive procedure utilized in medical imaging to evaluate blood flow through vasculature vessels, particularly the major arteries and veins in a body of the patient. Specifically, ultrasound waves continuously or intermittently transmitted into the body hit blood cells of the vasculature in motion whereby the pitch of the reflected sound waves changes (i.e., Doppler effect). The pitch changes are processed and displayed in different ways to enable a view of the resulting Doppler image to evaluate blood flow and diagnose any abnormalities which may lead to a stroke and/or heart failure (e.g., blocked/narrowing arteries, blood clots in veins, reduced blood flow, etc.). Examples of Doppler ultrasound tests as known in the art include a continuous wave ("CW") Doppler test, a pulse wave ("PW") Doppler test, a color Doppler test, a spectral Doppler test, a duplex Doppler test and a power Doppler test.

For optimal Doppler ultrasound, the transmitted ultrasound waves should be oblique to the direction of the blood flow to the greatest extent possible. However, due to the complex anatomy of the vasculature, the location of the tortuous blood vessels and the direction of blood flow are unknown prior to and/or during the transmission of the ultrasound waves. As a result, it is difficult to always position the ultrasound probe for oblique transmitted ultrasound waves to achieve optimal Doppler measurement display.

SUMMARY OF THE INVENTION

The present disclosure provides inventions utilizing Fiber-Optic RealShape ("FORS") sensing to enhance Doppler ultrasound.

For purposes of the inventions of the present disclosure, the term "Fiber-Optic RealShape ("FORS") sensor" broadly encompasses any type of optical fiber structurally configured as known in the art for extracting high density strain measurements of the optical fiber derived from light emitted into and propagated through the optical fiber and reflected back within the optical fiber in an opposite direction of the propagated light and/or transmitted from the optical fiber in a direction of the propagated light.

An example of a FORS sensor includes, but is not limited to, a multi-cored optical fiber structurally configured under the principle of Optical Frequency Domain Reflectometry (OFDR) for extracting high density strain measurements of the optical fiber derived from light emitted into and propagated through the optical fiber and reflected back within the optical fiber in an opposite direction of the propagated light and/or transmitted from the optical fiber in a direction of the propagated light via controlled grating patterns within the optical fiber (e.g., Fiber Bragg Gratings), a characteristic backscatter of the optical fiber (e.g., Rayleigh backscatter) or any other arrangement of reflective element(s) and/or transmissive element(s) embedded, etched, imprinted, or otherwise formed in the optical fiber.

Commercially and academically, Fiber-Optic RealShape may also be known as optical shape sensing ("OSS").

One form of the inventions of the present disclosure is a Doppler ultrasound system for executing a Doppler ultrasound test exemplary including, but not limited to, CW Doppler, PW Doppler, color Doppler, spectral Doppler, duplex Doppler and power Doppler. The Doppler ultrasound system employs an ultrasound probe, a vessel FORS sensor and a Doppler ultrasound controller. In operation, the ultrasound probe transmits an ultrasound beam through a bodily vessel (e.g., a blood vessel) for generating imaging data illustrative of an ultrasound image of fluid flow through the bodily vessel (e.g., blood flow through a blood vessel), and the vessel FORS sensor is introduced into the bodily vessel for generating vessel sensing data informative of a reconstructed shape of the vessel FORS sensor within the bodily vessel relative to the ultrasound probe. Responsive to the data, the Doppler ultrasound controller estimates a parametric relationship between the fluid flow through the bodily vessel and a transmission by the ultrasound probe of the ultrasound beam through the bodily vessel.

For purposes of the inventions of the present disclosure, the terms "Doppler ultrasound", "ultrasound probe", "ultrasound beam", "bodily vessel", "fluid flow", "imaging data", "ultrasound image", "sensing data", and "reconstructed shape" are to be interpreted as understood in the art of the present disclosure and as exemplary described herein.

For purposes of the inventions of the present disclosure, the terms "transmits", "generates", "reconstructs" and "estimates" and any word tenses thereof are to be interpreted as understood in the art of the present disclosure and as exemplary described herein.

For purposes of the inventions of the present disclosure, the term "parametric relationship" broadly encompasses one or more physical properties having value(s) determinative of characteristics or behavior of the physical relationship between the fluid flow through the bodily vessel and a transmission by the ultrasound probe of the ultrasound beam through the bodily vessel (e.g., distance, position, angle, etc.)

For purposes of the inventions of the present disclosure, the term "ultrasound probe" broadly encompasses any type of ultrasound probe known in the art including, but not limited to, ultrasound probes suitable for Doppler measurements of blood flow through a blood vessel.

For purposes of the present disclosure, the label "vessel" used herein for the term "FORS sensor" distinguishes the vessel FORS sensor from other FORS sensors as described and claimed herein without specifying or implying any additional limitation to the term "FORS sensor".

For purposes of the present disclosure, the label "vessel" used herein for the term "sensing data" distinguishes the vessel sensing data from other sensing data as described and claimed herein without specifying or implying any additional limitation to the term "sensing data".

For purposes of the present disclosure, the term "controller" broadly encompasses all structural configurations of an application specific main board or an application specific integrated circuit housed within or linked to a workstation for controlling an application of various inventive principles of the present disclosure as subsequently described herein.

The structural configuration of the controller may include, but is not limited to, processor(s), computer-usable/computer readable storage medium(s), an operating system, application module(s), peripheral device controller(s), slot (s) and port(s).

For purposes of the present disclosure, the label "Doppler ultrasound" used herein for the term "controller" distinguishes the Doppler ultrasound controller from others controllers as described and claimed herein without specifying or implying any additional limitation to the term "controller".

For purposes of the present disclosure, the term "workstation" broadly encompassed any type of workstation known in the art including, but not limited to, an assembly of one or more computing devices, a display/monitor, and one or more input devices (e.g., a keyboard, joysticks and mouse) in the form of a client computer, a desktop or a tablet.

For purposes of the present disclosure, the term "application module" broadly encompasses a component of the workstation consisting of an electronic circuit and/or an executable program (e.g., executable software and/firmware) for executing a specific application.

A second form of the inventions of the present disclosure is the Doppler ultrasound controller employing application modules in the form of a parameter estimation module and a Doppler measurement module. By structural design in operation, based on a registration between the ultrasound probe and the vessel FORS sensor, the parameter estimation module estimates the parametric relationship between the fluid flow through the bodily vessel (e.g., blood flow through a blood vessel) and the transmission by the ultrasound probe of the ultrasound beam through the bodily vessel. The Doppler measurement module derives a Doppler measurement of the fluid flow through the bodily vessel from the estimation by the parameter estimation module of the parametric relationship between the fluid flow through the bodily vessel and the transmission by the ultrasound probe of the ultrasound beam through the bodily vessel.

For purposes of the present disclosure, the label "parameter estimation" and "Doppler measurement" used herein for the term "module" distinguishes the different application modules as described and claimed herein without specifying or implying any additional limitation to the term "application module".

A third form of the inventions of the present disclosure is a Doppler ultrasound method involving the Doppler ultrasound controller, responsive to a generation by an ultrasound probe of imaging data and further responsive to a generation by a vessel FORS sensor of vessel sensing data, estimating a parametric relationship between a fluid flow through a bodily vessel (e.g., blood flow through a blood vessel) and a transmission by the ultrasound probe of an ultrasound beam through the bodily vessel based on a registration between the ultrasound probe and the vessel FORS sensor. The method further involves the Doppler ultrasound controller deriving a Doppler measurement of the fluid flow through the bodily vessel from the estimation of the parametric relationship between the fluid flow through the bodily vessel and the transmission by the ultrasound probe of the ultrasound beam through the bodily vessel.

The foregoing forms and other forms of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

BRIEF DESCRIPTION OF THE DRAWINGS

FIG. 4 illustrates an exemplary embodiment of a vessel FORS sensor in accordance with the inventive principles of the present disclosure.

FIG. 5 illustrates an exemplary embodiment of a probe FORS sensor in accordance with the inventive principles of the present disclosure.

FIG. 6 illustrates flowcharts representative of an exemplary Doppler ultrasound testing in accordance with the inventive principles of the present disclosure.

DETAILED DESCRIPTION OF THE PREFERRED EMBODIMENTS

Figure 1:
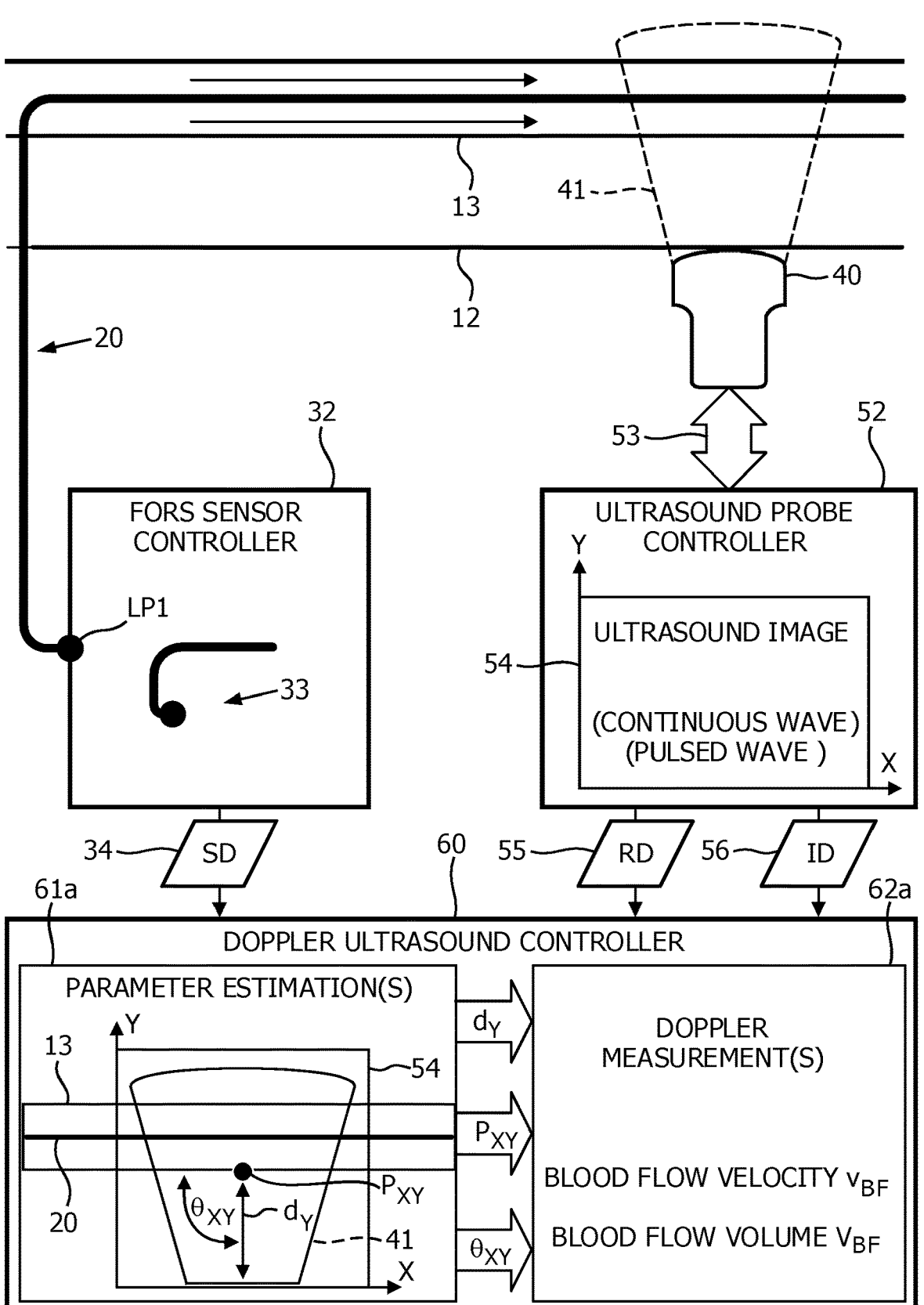
FIG. 1 illustrates a first exemplary embodiment of a Doppler ultrasound system in accordance with the inventive principles of the present disclosure.

The inventive principles of the present disclosure are premised on a FORS sensor being introduced into a bodily vessel, whereby a shape of the bodily vessel as well as a position and an orientation of the bodily vessel within an ultrasound image of the bodily vessel becomes known to a Doppler ultrasound controller for purposes of enhancing Doppler measurements of the fluid flow through the bodily vessel, particularly an estimation of a velocity and/or a volume of fluid flow through the bodily vessel. The following description of an execution of a Doppler ultrasound test by a Doppler ultrasound controller of the present disclosure for Doppler measurements of blood flow through a blood vessel as illustrated in FIG. 1 facilitates an understanding of the inventive principles of the present disclosure. From this description, those having ordinary skill in the art will appreciate how to apply the inventive principles of the present disclosure for making and using a Doppler ultrasound controller of the present disclosure for Doppler measurements of any form of fluid flow through any type of bodily vessel. Please note the various components of the present disclosure as shown in FIG. 1 are not drawn to scale, but drawn to conceptually visualize the inventive principles of the present disclosure Referring to FIG. 1, the Doppler ultrasound system employs a vessel FORS sensor 20, a FORS sensor controller 32, an ultrasound probe 40 (of any type), an ultrasound probe controller 52 and a Doppler ultrasound controller 60 for executing the Doppler ultrasound testing of a blood vessel 13.

Prior to the Doppler ultrasound testing of blood vessel 13, a positioning of vessel FORS sensor 20 relative to ultrasound probe 40 must be known. In practice, any registration technique known in the art may be implemented by ultrasound probe controller 52, Doppler ultrasound controller 60 or optionally by a dedicated registration controller (not shown) for registering vessel FORS sensor 20 to ultrasound probe 40. For example, as shown in FIG. 1, ultrasound probe controller 52 communicates registration data RD 55 informative of a registration of vessel FORS sensor 20 to ultrasound probe 40 by ultrasound probe controller 52.

Upon commencement of the Doppler ultrasound testing of blood vessel 13, vessel FORS sensor 20 is embedded into a medical device (e.g., a guide wire or a catheter) (not shown) or permanently encircled by a protective sleeve (not shown) for introduction into blood vessel 13 through a port of a skin 12 of a patient without any guidance or via any guidance technique known in the art (e.g., X-ray or ultrasound image guidance).

Concurrently and/or subsequently to the introduction of vessel FORS sensor 20 into blood vessel 13, FORS sensor controller 32 controls a generation of a reconstructed shape 33 of vessel FORS sensor 20 from a launch point LP1 to a distal end vessel FORS sensor 20 via any shape reconstruction technique known in the art. In practice, launch point LP1 is any point along vessel FORS sensor 20 between a proximal end and a distal end of FORS sensor 20, and may or may not coincide with a registration point along vessel FORS sensor 20. Based on the registration, FORS sensor 20 communicates sensing data 34 informative of a reconstructed shape 33 of vessel FORS sensor 20 within blood vessel 13 relative to ultrasound probe 40 to Doppler ultrasound controller 60.

Additionally, concurrently and/or subsequently to the introduction of vessel FORS sensor 20 into blood vessel 13, ultrasound probe controller 52 utilizes communication channels 53 with ultrasound probe 40 for controlling a transmission of ultrasound beam 41 and a reception by an echo beam (not shown) by ultrasound probe 40 via any known ultrasound wave technique known in the art (e.g., a continuous wave technique or a pulsed wave technique). From the received echo wave, ultrasound probe controller 52 generates imaging data 56 illustrative of an ultrasound image 54 of blood vessel 13 and communicates imaging data 56 to Doppler ultrasound controller 60. In practice, dependent of the scanning capabilities of ultrasound probe 40, ultrasound image 54 may be a XY two-dimensional planar image as shown, or alternatively, a XYZ three-dimensional volume image as known in the art From sensing data 34 and imaging data 56, a shape of blood vessel 13 as well as a position and an orientation of blood vessel 13 within ultrasound image 54 becomes known to Doppler ultrasound controller 60 for facilitating an execution of a parameter estimation 61a by Doppler ultrasound controller 60 of a parametric relationship between a blood flow through blood vessel 13 as symbolized by the arrows therein and a transmission by ultrasound probe 40 of ultrasound beam 41 through blood vessel 13. In practice, the parameter estimation 61a of such parametric relationship as shown may include, but is not limited to:

(1) a distance parameter $d_Y$ indicative of a distance of the blood flow through blood vessel 13 within ultrasound image 54 relative to ultrasound probe 40, (2) a position parameter $P_{XY}$ indicative of a position of the blood flow through blood vessel 13 within ultrasound image 54 relative to ultrasound probe 40, and (3) an angle parameter $\ominus_{XY}$ indicative of an angle between a direction of the blood flow through blood vessel 13 within ultrasound image 54 relative to ultrasound probe 40.

The estimated parameter relationship is estimated on a pixel-by-pixel basis of ultrasound image 54.

From the estimated parameter relationship, Doppler ultrasound controller 60 executes Doppler measurements 62a as known in the art of the blood flow through the blood vessel 13 including, but not limited to, an estimation as known in the art by Doppler ultrasound controller 60 of a velocity $v_{BF}$ and/or a volume $V_{BF}$ of blood flow through the blood vessel 13.

For example, Doppler ultrasound controller 60 may estimate velocity $v_{BF}$ of blood flow thorough the blood vessel 13 on a pixel-by-pixel basis of ultrasound image 54 in accordance with the following equation [1]:

$$v_{BF} = (f_D \times c)/(2 \times f_{cf} \times \cos \ominus_{XY}) \qquad [1]$$

where $f_{cf}$ is the frequency of ultrasound beam 40 in MHz,
where $f_D$ is the Doppler frequency of the echo beam in kHz,
where c is the speed of sound in tissue in m/sec, and
where $\ominus_{XY}$ is the estimated angle between the direction of ultrasound beam 41 and the blood flow through blood vessel 13.

By further example, Doppler ultrasound controller 60 may estimate blood flow volume $V_{BF}$ thorough the blood vessel 13 on a pixel-by-pixel basis of ultrasound image 54 in accordance with the following equation [2]:

$$V_{BF} = \tan\theta_{XY} \sum_{i=0}^{npix} v_i \Delta A \qquad [2]$$

where $\ominus_{XY}$ is the estimated angle between the direction of ultrasound beam 41 and the blood flow through blood vessel 13,
where $\Delta A$ is a pixel area of ultrasound image 54,
where $v_i$ is the measured blood flow velocity of each pixel, and
where npix is number of pixels.

From the Doppler measurements 62a, Doppler ultrasound controller 60 controls generation of a visual or graphical display of a Doppler image of blood vessel 13 as will be further explained herein. In practice, the display of the Doppler image may have any form known in the art including, but not limited to, a continuous wave ("CW") Doppler image, a pulsed wave ("PW") Doppler image, a color Doppler image, a spectral Doppler graph, and a duplex Doppler of the color Doppler image and spectral Doppler graph.

Still referring to FIG. 1, in practice, Doppler ultrasound controller 60 may be a stand-alone controller as shown or integrated with FORS sensor controller 32 and/or ultrasound probe controller 52.

Also in practice, ultrasound probe controller 52 may operate ultrasound probe 40 inclusive or exclusive of vessel FORS sensor 20 being within blood vessel 13.

Figure 2A:
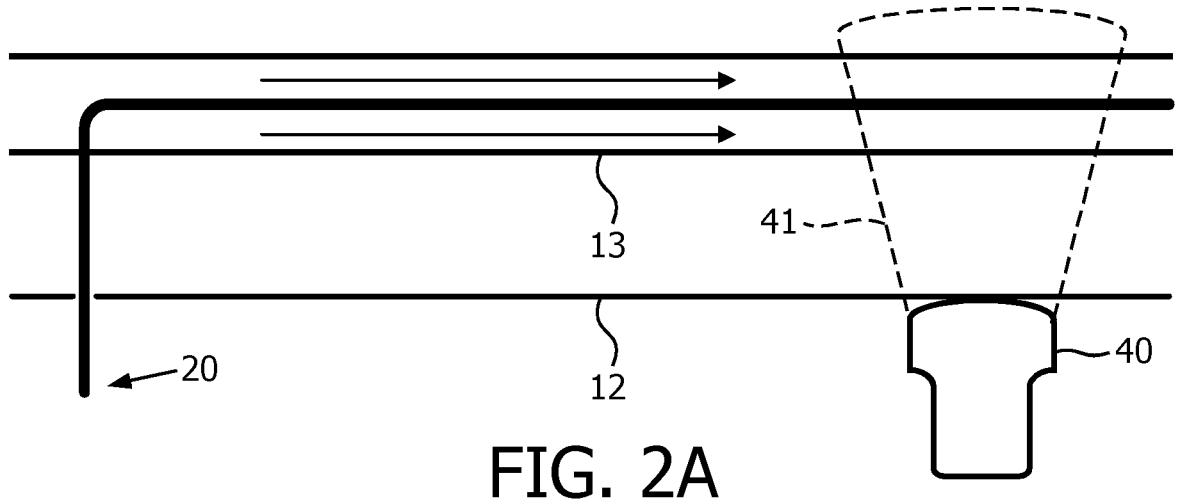
FIGS. 2A-2C illustrate exemplary positions of a vessel FORS sensor relative to an ultrasound beam in accordance with the inventive principles of the present disclosure.

For example, FIG. 2A illustrates vessel FORS sensor 20 within a portion of blood vessel 13 being imaged by ultrasound probe 40 via ultrasound beam 41.

Figure 2B:
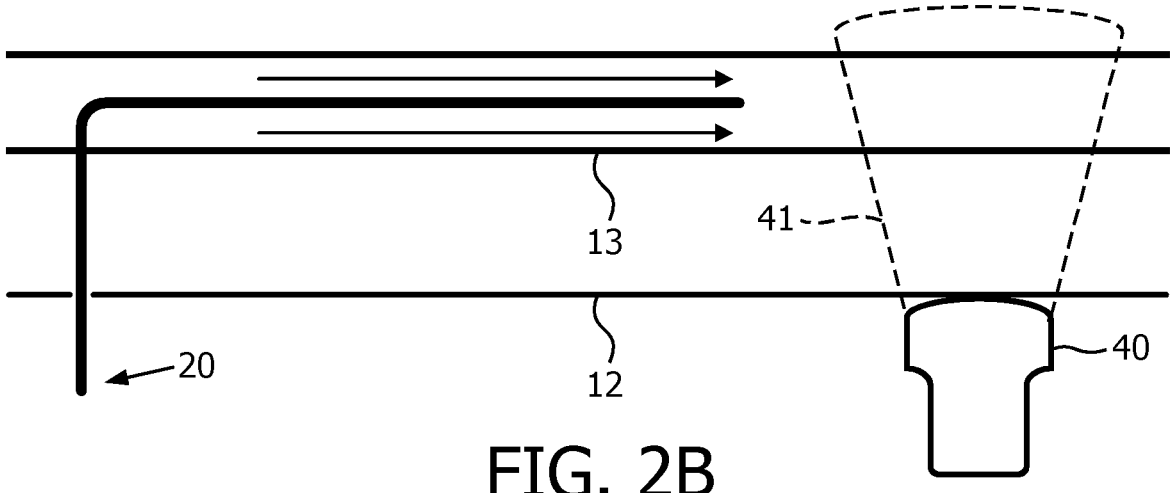

By further example, FIG. 2B illustrates vessel FORS sensor 20 within blood vessel 13, yet spaced from the portion of blood vessel 13 being imaged by ultrasound probe 40 via ultrasound beam 41 for purposes of minimizing any affect the presence of vessel FORS sensor 20 may have on the blood flow through the portion of blood vessel 13 being imaged by ultrasound probe 40.

Figure 2C:
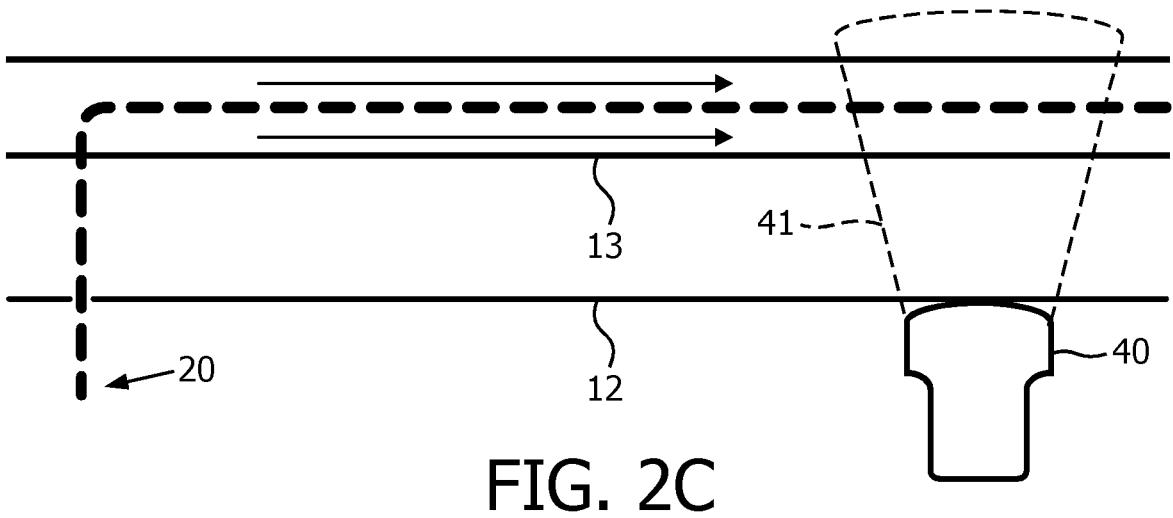

Also by example, FIG. 2C illustrates a recording of a previous position of vessel FORS sensor 20 within blood vessel 13 for purposes of eliminating any affect a presence of vessel FORS sensor 20 may have on the blood flow through the portion of blood vessel 13 being imaged by ultrasound probe 40 via ultrasound beam 41.

Referring back to FIG. 1, those having ordinary skill in the art will appreciate the enhanced Doppler measurements achieved by Doppler ultrasound controller 60 by the FORS sensing of blood vessel 13.

The following description of an execution of a Doppler ultrasound test by a Doppler ultrasound system of the present disclosure as illustrated in FIGS. 3-6 facilitates a further understanding of the inventive principles of the present disclosure. From this description, those having ordinary skill in the art will appreciate how to apply the inventive principles of the present disclosure for making and using a Doppler ultrasound system of the present disclosure. Please note the various components of the present disclosure as shown in FIGS. 3-6 are not drawn to scale, but drawn to conceptually visualize the inventive principles of the present disclosure.

Figure 3:
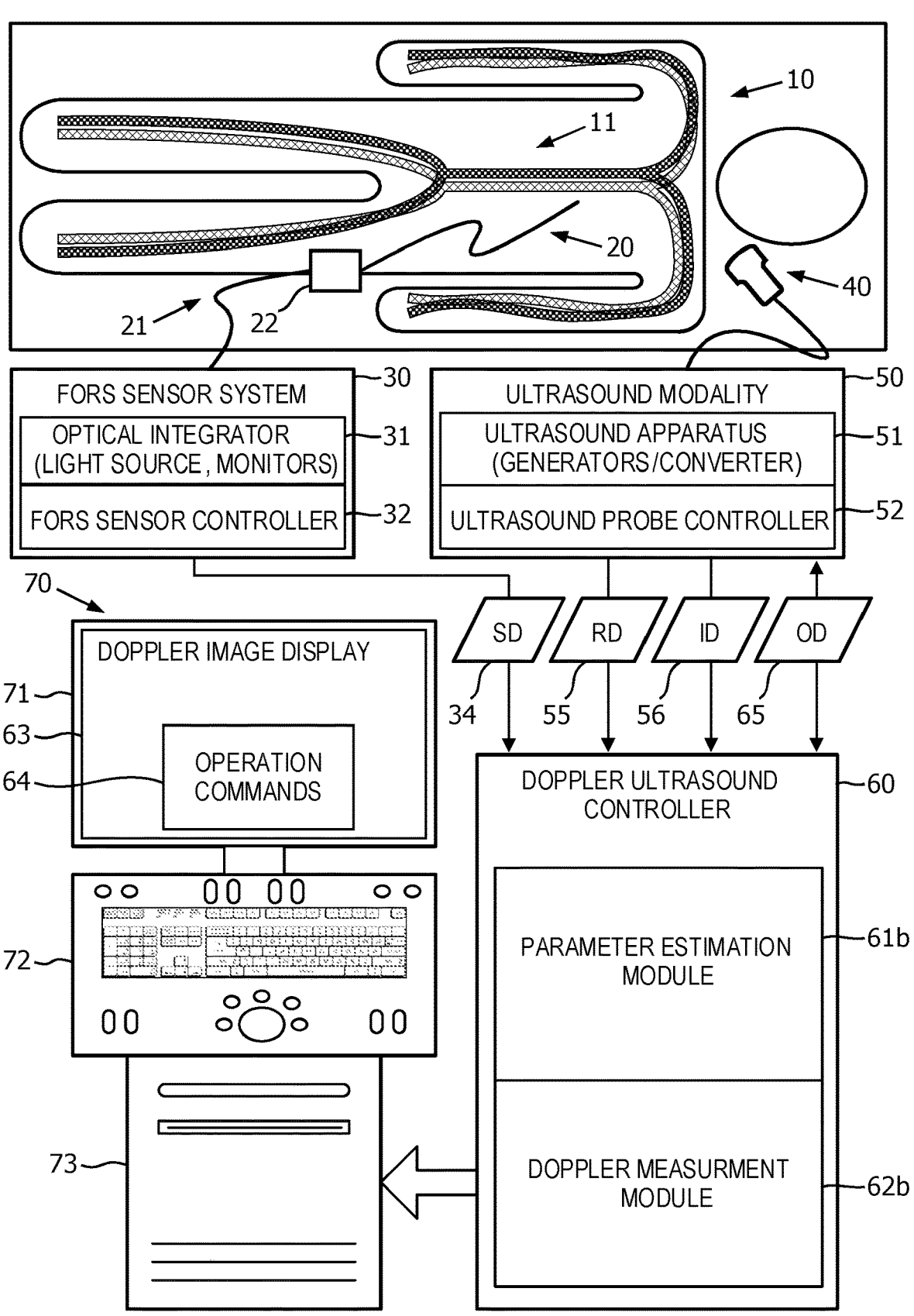
FIG. 3 illustrates a second exemplary embodiment of a Doppler ultrasound system in accordance with the inventive principles of the present disclosure.

Referring to FIG. 3, the Doppler ultrasound system of the present disclosure employs a universal FORS insert including vessel FORS sensor 20 (FIG. 1), an optical fiber 21 and a launch 22. The Doppler ultrasound system of the present disclosure further employs a FORS system 30, an ultrasound modality 50, a workstation 70 and Doppler ultrasound controller 60 (FIG. 1) installed on workstation 70.

Figures 4, 5, 6:
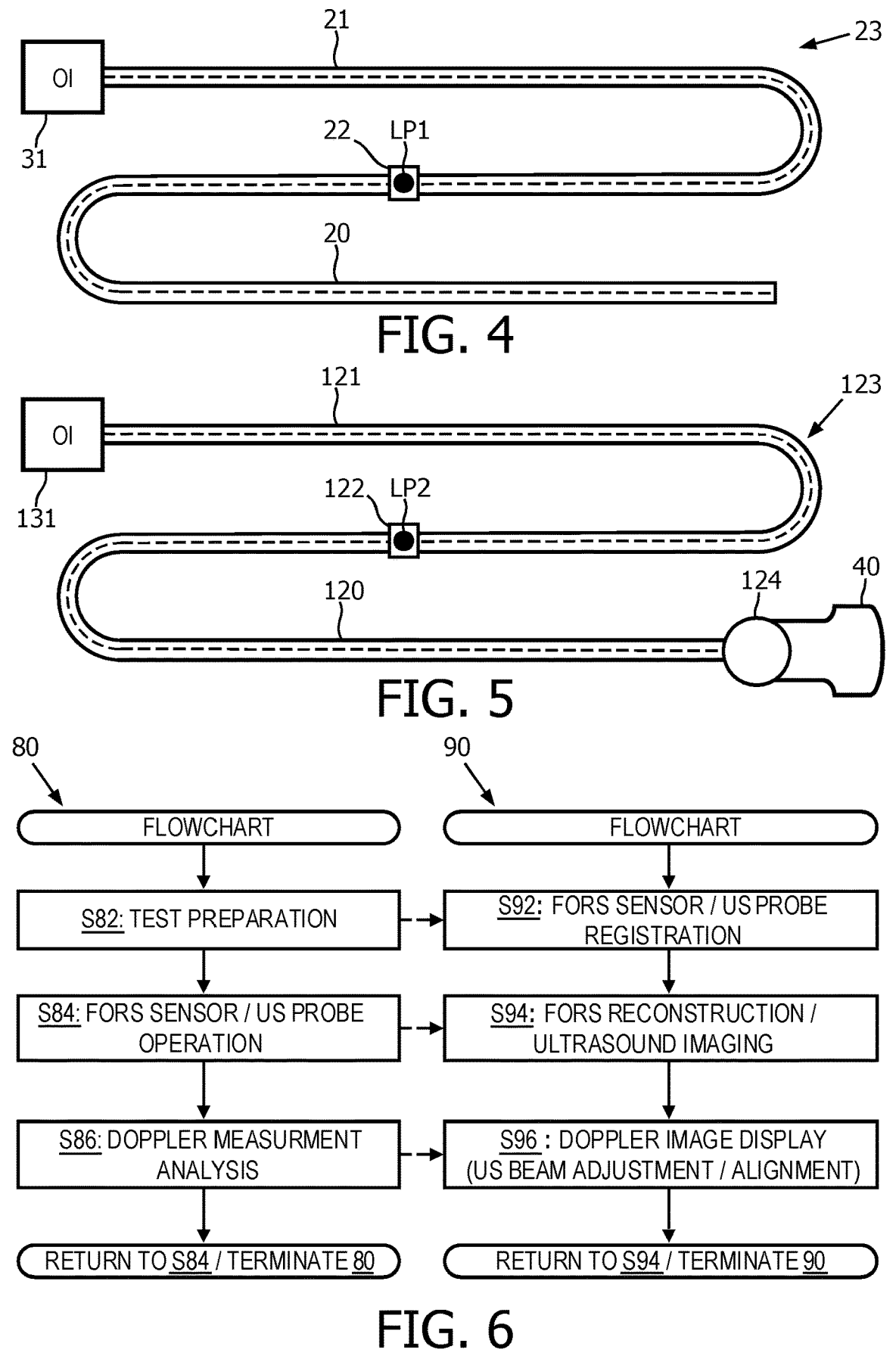

In one embodiment of an universal FORS insert 23 as shown in FIG. 4, vessel FORS sensor 20 is an optical fiber having controlled grating patterns within the optical fiber (e.g., Fiber Bragg Gratings), a characteristic backscatter of the optical fiber (e.g., Rayleigh backscatter) or any other arrangement of reflective elements and/or transmissive elements embedded, etched, imprinted, or otherwise formed in the optical fiber. In practice, the controlled gratings, characteristic backscatter, or reflective/transmissive elements may extend along any portion or an entirety of the optical fiber. Also in practice, the optical fiber may include of one or more individual fibers that may or may not be helixed.

In practice, the optical fiber of vessel FORS sensor 20 may be made partially or entirely of any glass, silica, phosphate glass or other glasses, or made of glass and plastic or plastic, or other materials used for making optical fibers. For impeding any damage to vessel FORS sensor 20 when introduced into the patient anatomy via manual or robotic insertion, the optical fiber of vessel FORS sensor 20 is embedded into a medical device (e.g., a guide wire or a catheter) or permanently encircled by a protective sleeve. In practice, the protective sleeve may be made from any flexible material of a specified hardness including, but not limited to, pebax, nitinol, furcation tubing, and stranded metal tubing. Also in practice, the protective sleeve may consist of two or more tubular components of sane or different degrees of flexibility and hardness in an overlapping and/or sequential arrangement.

In operation, vessel FORS sensor 20 distally extends from launch 22 and an optical fiber 21 proximally extends from launch 22 to an optical integrator 31. In practice, optical fiber 21 may be a separate optical fiber connected to vessel FORS sensor 20 at launch 22, or a proximal extension of vessel FORS sensor 20.

Furthermore, in an embodiment of an universal FORS probe 123 as shown in FIG. 5, a probe FORS sensor 120 has a proximal end adjoined to a launch 122 and a distal end adjoined to (e.g., connected, coupled, clamped, affixed, mounted, etc.) ultrasound probe 40 via an adjoining means 124. For this embodiment in practice, probe FORS sensor 120 is calibrated to ultrasound probe 40 as known in the art, and a shape of probe FORS sensor 120 is reconstructed as known in the art for purposes of tracking ultrasound probe 40.

In operation, probe FORS sensor 120 distally extends from launch 122 and an optical fiber 121 proximally extends from launch 122 to an optical integrator 131. In practice, optical fiber 121 may be a separate optical fiber connected to probe FORS sensor 120 at launch 122, or a proximal extension of probe FORS sensor 120.

Referring back to FIG. 3, in one embodiment as known in the art, FORS sensor system 30 (FIG. 3) includes optical integrator 31 (FIG. 3) and FORS controller 32 (FIG. 1) directing a broadband optical source of optical integrator 31 for emitting a light into a vessel FORS sensor 20 whereby a reflection wavelength monitor of optical integrator 31 monitors all reflection of the propagated light back by vessel FORS sensor 20 and/or a transmission wavelength monitor of optical integrator 31 (FIG. 3) monitors all transmission of the propagated light by vessel FORS sensor 20. From the reflected and/or transmitted light, FORS controller 32 controls a communication to Doppler ultrasound controller 60 of sensing data ("SD") 34 informative of a shape of vessel FORS sensor 20 within a frame coordinate system referenced by launch 22 and registered to ultrasound probe 40 to facilitate a generation of a reconstructed shape of vessel FORS 20.

In practice, launch 22 may be fixed to a point in the room, such as, for example, a surgical rail of an operating table as shown or a patient 10.

If probe FORS sensor 120 as shown in FIG. 5 is utilized, then the Doppler ultrasound system further employs an optical integrator 131 corresponding to optical integrator 31 for purposes of tracking ultrasound probe 40. More particularly, FORS controller 32 (FIG. 1) controls a broadband optical source of optical integrator 131 for emitting a light into probe FORS sensor 120 whereby a reflection wavelength monitor of optical integrator 131 monitors all reflection of the propagated light back by probe FORS sensor 120 and/or a transmission wavelength monitor of optical integrator 131 monitors all transmission of the propagated light by probe FORS sensor 120. From the reflected and/or transmitted light, FORS controller 32 controls a communication to Doppler ultrasound controller 60 of sensing data informative of a shape of probe FORS sensor 120 within a frame coordinate system referenced by launch 122 and calibrated to ultrasound probe 40.

Referring back to FIG. 3, in one embodiment known in the art, ultrasound modality 50 employs an ultrasound apparatus 51 for operating ultrasound probe 40 in imaging a vasculature 11 of patient 10 as controlled by ultrasound probe controller 52 (FIG. 1), which communicates imaging data 56 to Doppler ultrasound controller 60. More particularly, ultrasound apparatus 51 may include a known arrangement of a wave generator (e.g., continuous or pulse), a scan generator, an amplifier and a scan converter controllable by ultrasound probe controller 52 as known in the art.

Workstation 70 includes a known arrangement of a monitor 71, a keyboard 72 and a computer 73.

Doppler ultrasound controller 60 includes an application module in the form of a parameter estimation module 61*b* for estimating the parametric relationship between a blood flow through a vessel of a vasculature 11 and a transmission by the ultrasound probe 40 of an ultrasound beam through the vessel of vasculature 11 as exemplary shown in FIG. 1.

Referring back to FIG. 3, Doppler ultrasound controller 60 further includes an application module in the form of a Doppler measurement module 62*b* for executing a Doppler measurement of the blood flow through the vessel of vasculature 11 derived from an estimated parametric relationship as exemplary shown in FIG. 1.

Doppler measurement module 62*b* also executes a control of a display 63 of a Doppler image of the vessel of vasculature 11 as known in the art (e.g., a CW Doppler image, a PW Doppler image, a color Doppler image, a spectral Doppler graph, and a duplex Doppler of the color Doppler image and spectral Doppler graph). Display 63 of the Doppler image is enhanced by Doppler measurements derived from the estimated parametric relationship.

To this end, in practice, Doppler measurement module 62*b* and ultrasound probe controller 52 may exchange operational data ("OD") 64 indicative of operational parameters of ultrasound probe 40 (e.g., transmit frequency, power and size) and inclusive of commands from Doppler measurement module 62*b* for controlling the transmission of the ultrasound beam by ultrasound probe 40. Such commands from Doppler measurement module 62B provide for an optimization of the estimated parametric relationship.

Figures 7A, 7B, 7C:
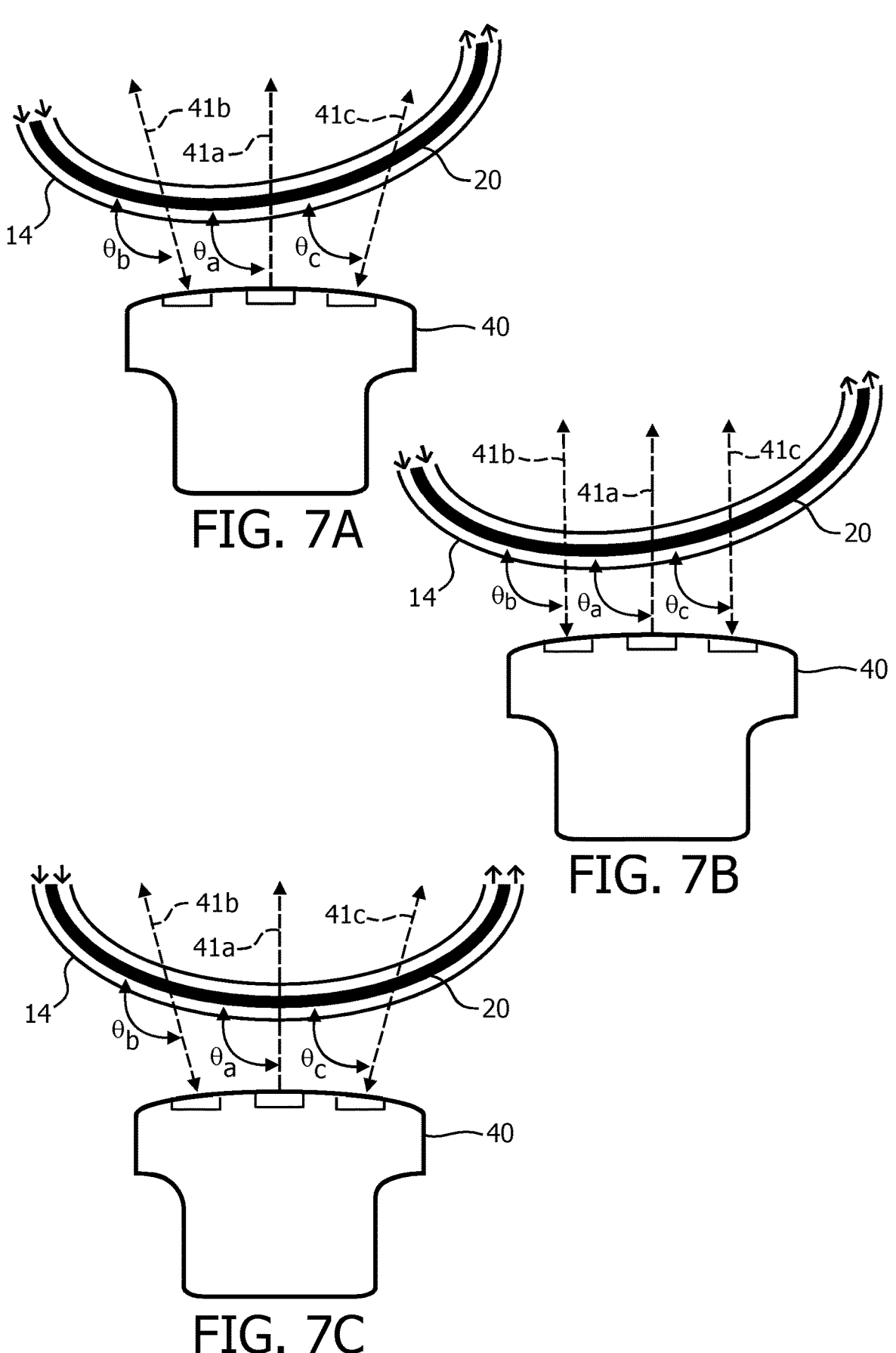
FIGS. 7A-7C illustrate exemplary ultrasound scanning of a tortuous blood vessel in accordance with the inventive principles of the present disclosure.

For example, a vessel 14 of vasculature may have a tortuous shape as shown in FIG. 7A whereby pulses 41*a*-41*c* of ultrasound beam 41 have different angles $\ominus_a$, $\ominus_b$ and $\ominus_c$, with different sections of vessel 14. As such, Doppler measurement module 62*b* may execute appropriate signal processing/filter techniques as known in the art (e.g., a normalization technique) that realigns pulses 41*a*-41*c* as shown in FIG. 7B to remove the effect of the different angles $\ominus_a$, $\ominus_b$ and $\ominus_c$.

Referring back to FIG. 3, alternative to commanding ultrasound probe controller 52, Doppler measurement module 62*b* may control a further display 64 of operation commands (e.g., a textual, visual and/or graphical information) of an operation of ultrasound probe 40 to optimize the Doppler image of the vessel of vasculature 11. Such commands may be for the realignment of pulses of the ultrasound beam as exemplary shown in FIGS. 7A and 7B and/or may be for an adjustment to a positioning of ultrasound probe 40 relative to the vessel of vasculature 11 as exemplary shown in FIGS. 7A and 7C.

An exemplary workflow of a Doppler ultrasound method of the present disclosure will now be described herein.

Referring to FIG. 6, flowcharts 80 and 90 are an application of the workflow in the context of an ultrasound technician executing a Doppler ultrasound involving the Doppler ultrasound system as shown in FIG. 3. Flowchart 80 represents actions performed by a ultrasound technician during the Doppler ultrasound testing, and flowchart 90 represents actions executed by the Doppler ultrasound system as shown in FIG. 3 as directed by the ultrasound technician.

Referring to FIGS. 3 and 6, a stage S82 of flowchart 80 involves the ultrasound technician preparing for the Doppler ultrasound testing by (1) positioning patient 10 prone on the operating table, (2) performing necessary actions for calibrating a probe FORS sensor 120 (FIG. 5) to ultrasound probe 40 if sensor 120 is to be utilized during the testing for tracking ultrasound probe 40, and (3) performing necessary actions for registering vessel FORS sensor 20 to ultrasound probe 40 as previously described herein.

Stage S82 further involves the ultrasound technician interfacing with ultrasound probe controller 52 (or alternatively with a registration module) dependent upon the particular registration technique (and calibration technique) to be executed during a stage S92 of flowchart 90 for the registration of vessel FORS sensor 20 to ultrasound probe 40.

Upon completion of the testing preparation, a stage S84 of flowchart 80 involves the ultrasound technician performing the test by (in no particular order):

(1) introducing vessel FORS sensor 20 into a vessel of vasculature 11 of patient 10, and (2) positioning ultrasound probe for imaging the vessel of vasculature 11 of patient 10.

Stage S84 further involves the ultrasound technician interfacing FORS sensor controller 32 and ultrasound probe controller 52 during a stage S94 of flowchart 90 for reconstructing the shape of vessel FORS sensor 20 and generating the ultrasound image of the vessel of vasculature 11 of patient 10. During stage S94, Doppler measurement module 62*b* (FIG. 3) may optimize the generation of the ultrasound image 63 as previously described herein (e.g., command a realignment by ultrasound probe controller 52 of pulses of the ultrasound beam).

Concurrent or subsequent to stages S84 and S94, a stage S86 of flowchart 80 involves the ultrasound technician analyzing a display 63 during a stage S96 of flowchart 90 of a Doppler ultrasound image controlled by Doppler measurement module 62*b* as previously described herein. Doppler measurement module 62*b* may further control a display 64 of operation commands (e.g., a textual, visual and/or graphical information) to optimize the Doppler image of the vessel of vasculature 11 as previously described herein (e.g., command(s) for realignment of pulses of the ultrasound beam and/or for adjusting a positioning of ultrasound probe 40 relative to the vessel of vasculature 11).

Upon the initial Doppler imaging analysis and display, flowcharts 80 and 90 may be terminated or returned to stages S84 and S94 for further operation of vessel FORS sensor 20 and operation of ultrasound probe 40.

More particularly, referring to FIGS. 1-7, those having ordinary skill in the art will appreciate numerous benefits of the inventions of the present disclosure including, but not limited to, enhanced Doppler measurements of a vasculature vessel.

More particularly, as previously described herein, a direction in which ultrasound is sent impacts the ability to record a good Doppler measurement. Due to complex vasculature, often the direction of blood vessels isn't known. This results in sub-optimal Doppler measurements. With the inventions of the present disclosure, FORS sensing provides information about the location of a bodily vessel (e.g., a blood vessel) and in turn fluid flow through the bodily vessel (e.g., blood flow through the blood vessel), which allows for ultrasound to be transmitted optimally and measuring better Doppler readings.

Also, if a vasculature vessel is tortuous (which is often the case), ultrasound has to be transmitted differently to different regions (e.g., transmitted at different angles). FORS sensing of the present disclosure provides a reconstruction of a partial or full shape of the vasculature vessel whereby ultrasound transmit parameters (e.g., transmit angles) may be optimized for different parts of the vasculature vessel.

Further, as one having ordinary skill in the art will appreciate in view of the teachings provided herein, features, elements, components, etc. described in the present disclosure/specification and/or depicted in the Figures may be implemented in various combinations of hardware and software, and provide functions which may be combined in a single element or multiple elements. For example, the functions of the various features, elements, components, etc.

shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of novel and inventive Fiber Optic RealShape sensing for enhancing Doppler measurements, (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A Doppler ultrasound system, comprising:
an ultrasound probe configured to transmit an ultrasound beam through a bodily vessel from outside the bodily vessel for generating imaging data illustrative of an ultrasound image of a fluid flow, having a flow direction and velocity, through the bodily vessel;

a vessel optical shape sensing (OSS) sensor configured to be introduced into the bodily vessel for generating vessel sensing data;
an OSS controller configured to generate a reconstructed shape of the vessel OSS sensor within the bodily vessel relative to the ultrasound probe from the vessel sensing data; and
a Doppler ultrasound controller for controlling a Doppler measurement of the fluid flow through the bodily vessel in response to the imaging data generated by the ultrasound probe and the reconstructed shape of the vessel OSS sensor,
wherein the Doppler ultrasound controller is configured to estimate a parametric relationship between the fluid flow through the bodily vessel and a transmission by the ultrasound probe of the ultrasound beam through the bodily vessel based on a registration between the ultrasound probe and the vessel OSS sensor, and
wherein the Doppler ultrasound controller is further configured to derive the Doppler measurement of the fluid flow through the bodily vessel from the estimated parametric relationship between the fluid flow through the bodily vessel and the transmission by the ultrasound probe of the ultrasound beam through the bodily vessel.

2. The Doppler ultrasound system of claim 1, wherein the Doppler measurement estimates at least one of a velocity or a volume of the fluid flow through the bodily vessel.

3. The Doppler ultrasound system of claim 1, wherein the Doppler ultrasound controller is further configured to control a display of a Doppler image showing the Doppler measurement of the fluid flow through the bodily vessel.

4. The Doppler ultrasound system of claim 1, wherein the Doppler ultrasound controller is further configured to control a user communication of least one of an adjustment of the ultrasound probe relative to the bodily vessel and a realignment of the transmission by the ultrasound probe of the ultrasound beam through the bodily vessel.

5. The Doppler ultrasound system of claim 1, wherein the Doppler ultrasound controller is further configured to control the transmission by the ultrasound probe of the ultrasound beam through the bodily vessel.

6. The Doppler ultrasound system of claim 1, further comprising:
a probe OSS sensor calibrated to the ultrasound probe for generating probe sensing data informative of a reconstructed shape of the probe OSS sensor relative to the ultrasound probe,
wherein the Doppler ultrasound controller is further configured to estimate the parametric relationship between the fluid flow through the bodily vessel and the transmission by the ultrasound probe of the ultrasound beam through the bodily vessel further based on a calibration of the probe OSS sensor to the ultrasound probe.

7. The Doppler ultrasound system of claim 1, wherein the imaging data generated by the ultrasound probe is inclusive of the vessel OSS sensor within the bodily vessel.

8. The Doppler ultrasound system of claim 1, wherein the imaging data generated by the ultrasound probe is exclusive of the vessel OSS sensor within the bodily vessel.

9. A Doppler ultrasound system, comprising:
an ultrasound probe configured to transmit an ultrasound beam through a bodily vessel from outside the bodily vessel for generating imaging data illustrative of an ultrasound image of a fluid flow through the bodily vessel;

13 a vessel optical shape sensing (OSS) sensor configured to be introduced into the bodily vessel for generating vessel sensing data;

an OSS controller configured to generate a reconstructed shape of the vessel OSS sensor within the bodily vessel relative to the ultrasound probe from the vessel sensing data; and a Doppler ultrasound controller for controlling a Doppler measurement of the fluid flow through the bodily vessel in response to the imaging data generated by the ultrasound probe and the reconstructed shape of the vessel OSS sensor, wherein the Doppler ultrasound controller is configured to estimate a parametric relationship between the fluid flow through the bodily vessel and a transmission by the ultrasound probe of the ultrasound beam through the bodily vessel based on a registration between the ultrasound probe and the vessel OSS sensor, wherein the Doppler ultrasound controller is further configured to derive the Doppler measurement of the fluid flow through the bodily vessel from the estimated parametric relationship between the fluid flow through the bodily vessel and the transmission by the ultrasound probe of the ultrasound beam through the bodily vessel, and wherein the parametric relationship between the fluid flow through the bodily vessel and the transmission by the ultrasound probe of the ultrasound beam through the bodily vessel includes at least an angle parameter indicative of an angle between a direction of the fluid flow through the bodily vessel within the ultrasound image relative to a direction of the ultrasound beam transmitted by the ultrasound probe.

10. The Doppler ultrasound system of claim 9, wherein the parametric relationship between the fluid flow through the bodily vessel and the transmission by the ultrasound probe of the ultrasound beam through the bodily vessel further includes at least one of:

a distance parameter indicative of a distance of the fluid flow through the bodily vessel within the ultrasound image relative to the ultrasound probe; or a position parameter indicative of a position of the fluid flow through the bodily vessel within the ultrasound image relative to the ultrasound probe.

11. The Doppler ultrasound system of claim 9, wherein the Doppler measurement estimates at least one of a velocity or a volume of the fluid flow through the bodily vessel.

12. The Doppler ultrasound system of claim 9, wherein the Doppler ultrasound controller is further configured to control a display of a Doppler image showing the Doppler measurement of the fluid flow through the bodily vessel.

13. The Doppler ultrasound system of claim 9, wherein the Doppler ultrasound controller is further configured to control a user communication of least one of an adjustment of the ultrasound probe relative to the bodily vessel and a realignment of the transmission by the ultrasound probe of the ultrasound beam through the bodily vessel.

14. The Doppler ultrasound system of claim 9, wherein the Doppler ultrasound controller is further configured to control the transmission by the ultrasound probe of the ultrasound beam through the bodily vessel.

\* \* \* \* \*